(12) United States Patent
Sordo et al.

(10) Patent No.: US 11,992,584 B2
(45) Date of Patent: May 28, 2024

(54) DEVICE FOR DIFFUSION OF VOLATILE SUBSTANCES

(71) Applicant: ZOBELE HOLDING, S.P.A., Trento (IT)

(72) Inventors: Livio Sordo, Trento (IT); Cedric Morhain, Barcelona (ES); Stefano Deflorian, Trento (IT)

(73) Assignee: ZOBELE HOLDING, S.P.A. (IT)

( * ) Notice: Subject to any disclaimer, the term of this patent is extended or adjusted under 35 U.S.C. 154(b) by 6 days.

(21) Appl. No.: 16/956,629

(22) PCT Filed: Dec. 20, 2018

(86) PCT No.: PCT/EP2018/086255
§ 371 (c)(1),
(2) Date: Jun. 22, 2020

(87) PCT Pub. No.: WO2019/122163
PCT Pub. Date: Jun. 27, 2019

(65) Prior Publication Data
US 2020/0397938 A1    Dec. 24, 2020

(30) Foreign Application Priority Data

Dec. 22, 2017 (EP) ..................... 17210018

(51) Int. Cl.
*A61L 9/12* (2006.01)
*B01D 50/00* (2022.01)

(52) U.S. Cl.
CPC ............... *A61L 9/12* (2013.01); *B01D 50/00* (2013.01); *A61L 2209/131* (2013.01)

(58) Field of Classification Search
CPC ............... A61L 9/12; A61L 9/04; B01D 50/00

USPC .......................................................... 239/34
See application file for complete search history.

(56) References Cited

U.S. PATENT DOCUMENTS

| 4,356,969 A | * | 11/1982 | Obermayer | ......... A01M 1/2044 239/6 |
| 4,917,301 A | * | 4/1990 | Munteanu | .................. A61L 9/01 239/45 |
| 5,497,942 A | * | 3/1996 | Zingle | ..................... A61L 9/042 428/905 |

FOREIGN PATENT DOCUMENTS

| WO | WO 2013/014078 A1 | 1/2013 |
| WO | WO 2016/187274 A1 | 11/2016 |

OTHER PUBLICATIONS

International Search Report dated Feb. 21, 2019 in corresponding PCT International Application No. PCT/EP2018/086255.
(Continued)

*Primary Examiner* — Robert A Hopkins
(74) *Attorney, Agent, or Firm* — OSTROLENK FABER LLP

(57) ABSTRACT

A device for diffusion of volatile substances that includes a container for containing volatile substances, including the container, an aperture defining a sealing area, and a multi-layer structure placed on the aperture. The multilayer structure includes a microporous membrane through which the volatile substances are diffused and a barrier layer that is removed before a first use. The multilayer structure also includes a sealing portion in contact with the sealing area. A device with a microporous membrane where the porosity of the membrane at the portion of the sealing area has been substantially reduced or eliminated to stop liquid transportation.

8 Claims, 1 Drawing Sheet

(56) References Cited

OTHER PUBLICATIONS

Written Opinion dated Feb. 21, 2019 in corresponding PCT International Application No. PCT/EP2018/086255.

* cited by examiner

DEVICE FOR DIFFUSION OF VOLATILE SUBSTANCES

CROSS-REFERENCE TO RELATED APPLICATIONS

The present application is a 35 U.S.C. §§ 371 national phase patent application based on PCT/EP2018/086255, filed Dec. 20, 2018, which claims priority to European Patent Application No. 17210018.2, filed Dec. 22, 2017, the entire contents of both applications being incorporated herein by reference. The PCT International Application was published in the English language.

The present invention refers to a device for diffusion of volatile substances, comprising a container with a sealing area, that guarantees a better stability during its storage.

BACKGROUND OF THE INVENTION

Membrane air fresheners have been growing a lot in the air freshener market.

Most common system are based on polyolefin monolithic membrane (i.e. non-microporous) that gives an acceptable behavior but has limited efficiency and also limits a lot the kind of volatile substances or perfume that can be used.

This kind of membrane is very easy to produce as the membrane comes in a multilayer structure together with a barrier material. The multilayer is sealed on an aperture of a container containing the volatile substances or fragrance in a single step. Before a first use, the barrier is removed by pealing by the user.

Several intents have been done in using membrane with a much higher transportation rate of fragrances. The issue here is that if the transportation through the membrane wall is higher, it is also higher through the sealing area defined in the aperture of the container, and thus during storage we observe that the portion of the membrane in contact with the sealing are is evaporating slightly.

A special kind of recently implemented membranes are microporous systems. Being a micro porous system that works by capillarity, the portion in contact with the sealing are is able to transport the liquid without any limitations along distances of several millimeters, and so the sealing area is a quite open system, that is a problem to guarantee refill stability during storage.

Therefore, it is evident the need of a device for diffusion of volatile substances, comprising a container with a sealing area, that guarantees a better stability during its storage.

DESCRIPTION OF THE INVENTION

With the device according to the invention said drawbacks can be solved, presenting other advantages that will be described hereinafter.

The device for diffusion of volatile substances according to present invention comprises:
- a container for containing volatile substances, including the container an aperture defining a sealing area; and
- a multilayer structure placed on said aperture, said multilayer structure comprising a microporous membrane through which the volatile substances are diffused and a barrier layer that is removed before a first use;

wherein said multilayer structure also comprises a sealing portion in contact with said sealing area.

Advantageously, said sealing portion is made from a polymeric material, such as e.g. from thermoset resin or thermoplastic, and it is preferably welded to said sealing area.

Furthermore, the material of said sealing portion is introduced into the pores of the microporous membrane in a pattern corresponding to the sealing area, sealing these pores.

According to a preferred embodiment, said sealing area is a perimetric flange in the perimeter of said aperture of the container.

Furthermore, preferably said multilayer structure also comprises a separation layer than is placed between the barrier layer and the membrane, and that is removed before a first use.

Said barrier layer can be made from metal or plastic, and said separation layer can be made from paper or plastic.

According to the invention, it is provided a device with a microporous membrane where the porosity of the membrane at the portion of the sealing area has been substantially reduced or eliminated to stop liquid transportation.

BRIEF DESCRIPTION OF THE DRAWINGS

For a better understanding of what has been disclosed, some drawings are attached in which, diagrammatically and only as a non-limitative example a specific embodiment is shown.

DESCRIPTION OF A PREFERRED EMBODIMENT

Figure 1:
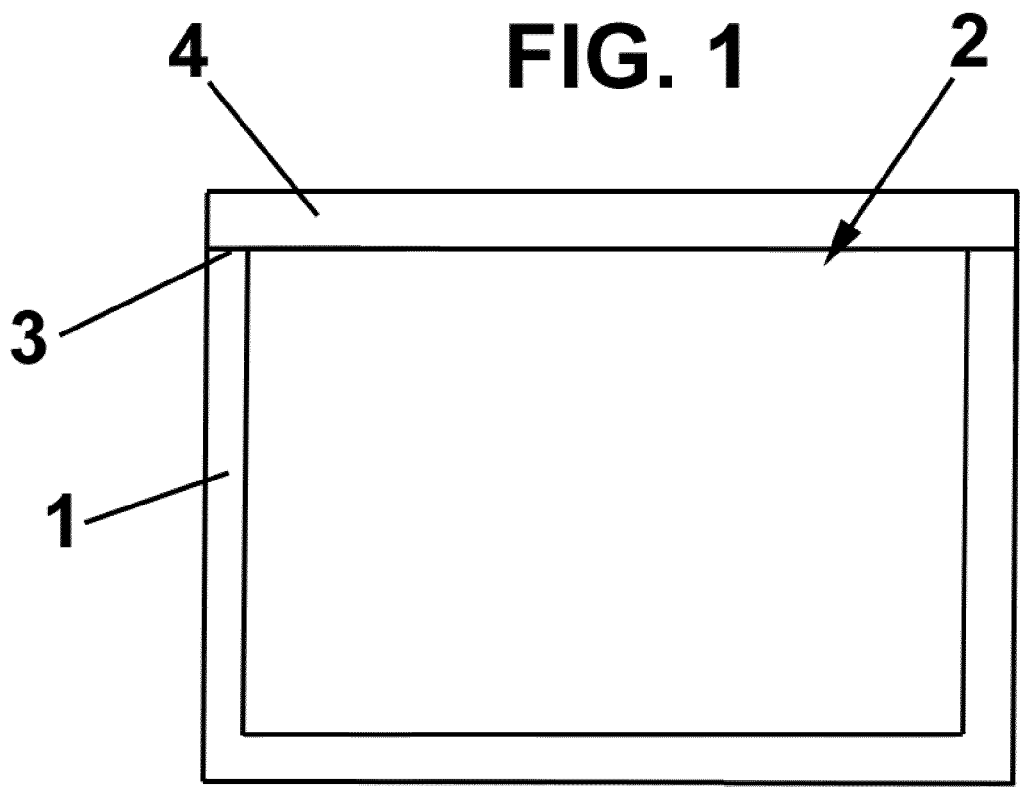
FIG. 1 is a cross-section diagrammatical elevation view of the device according the present invention.
Figure 2:
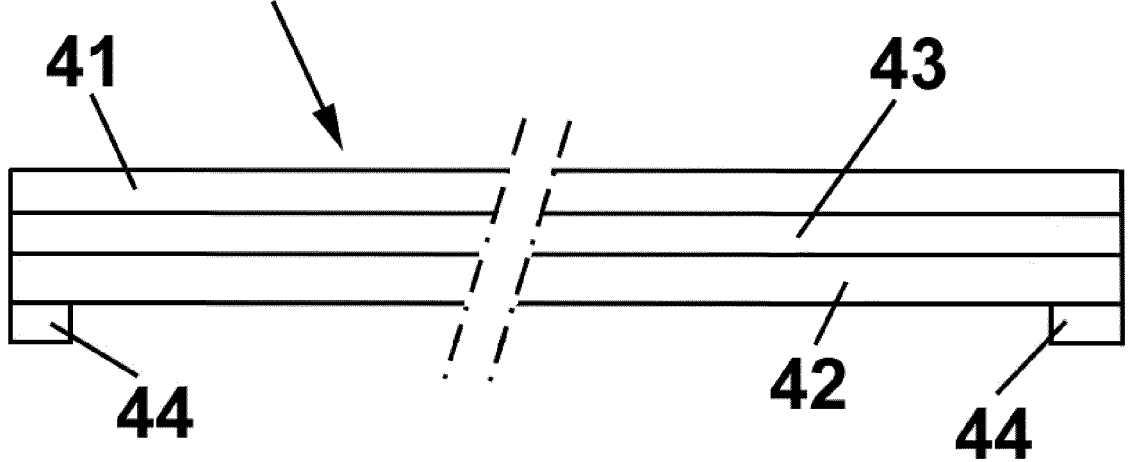
FIG. 2 is a cross-section detail of the contact zone between the multilayer structure and the container.

The device according to the present invention comprises a container 1, preferably thermoformed, filled with the volatile substances, such as a liquid.

The container 1 includes an aperture 2 defining a sealing area 3, such as e.g. a perimetric flange.

On this aperture 2 a multilayer structure 4 is placed, e.g. by welding, preferably heat welding. This multilayer structure 4 comprises, according to the shown embodiment, a barrier layer 41, a microporous membrane 42 and a separation layer 43, which is interposed between the barrier layer 41 and the separation layer 43.

Before a first use, user removes the barrier layer 41 by pealing it, and the barrier layer 41 separates from the membrane 42 thanks to the separation layer 43.

Preferably, the separation layer 43 is a layer with low internal cohesive mechanical resistance and will separate along its thickness, remaining part of this layer 43 on the membrane 42 and part on the barrier layer 41. E.g., the separation layer 43 can be a paper layer. Alternatively, the separation layer 43 can be made from a plastic having a reduced adhesion on the membrane.

By "reduced" it is understood that the strength of adhesion between separation layer 43 and the membrane 42 is high enough to keep it in place during storage and before first use, but low enough to allow the separation when user pull the barrier layer 41 and the separation layer 43 of the multilayer structure 4.

It will be clear for a person skilled in the art that the mechanical resistance of the adhesion between membrane 42 and separation layer 43 shall be lower than the mechanical resistance of the membrane 42 and of the barrier layer 41 and it will be low enough to not require an external tool to separate the layers.

The membrane 42 is made of a microporous membrane, e.g. made of polyethylene, polypropylene, ultra-high molecular weight polyethylene, or polytetrafluoroethylene, although it will be clear that any known microporous material can be used.

The barrier layer 41 is made from a material having high barrier properties to the volatile substance, preferably aluminium, and a plastic layer to reinforced mechanically, preferably a PET layer.

This multilayer structure 4 comprises also a sealing portion 44 in correspondence with the sealing area 3 in order to improve the refill integrity during storage by reducing liquid transportation along the plane of the multilayer structure 4.

This sealing portion 44 can be a ribbon of polymeric material on the membrane 42 side of the multilayer structure 4 in an area that will be placed in coincidence with the sealing area 3 of the container 1 to be made with that membrane 42.

The polymeric material of the sealing portion 44 penetrates into the pores during the attachment of the multilayer structure 4 to the container 1, and then the polymeric material solidifies.

Two main options exist to implement the invention, that differs mainly of the kind of polymeric material that is used for the sealing portion 44, that can be a thermoset resin or a thermoplastic resin.

If the sealing portion 44 is a thermoset resin, it is applied in liquid state on the surface of the membrane 42 in an area that will later corresponds to the sealing area 3 of the container 1.

Depending of the viscosity of that resin, it may be able to penetrate inside the membrane 42 without the need to apply a certain pressure on it. Alternatively, the material penetration through the membrane 42 can be forced by applying a mechanical stress on the sealing portion 44. This could be achieved by calendaring the membrane 42 after the deposition of the sealing portion 44.

As an example, the container 1 can be made from PET/EVOH/PE with a thickness of 500 microns, and the multilayer structure 4 can be made of a membrane 42 of microporous polyethylene with a thickness of 50 microns, a separation layer 41 with a thickness of 100 microns of PP, and on top of the PP layer an aluminium sheet of 20 microns of thickness and a PET sheet with a thickness of 20 microns (external side).

The thermoset sealing portion 44 is deposed on the external side of the membrane 42 along a pattern. The width of the sealing portion 44 is 1 mm and its thickness is 0.2 mm The thermoset material is preferably of the kind of epoxy or acrylic glue, UV curable. An UV light is applied to the glue between application of the glue and the welding of the multilayer structure 41 on the container 1. It would be clear for a person skilled in the art that any known thermoset having the sufficient chemical resistance to the volatile substances to be diffused can be used.

Optionally, a second dose of UV can be applied after the welding to complete the glue curing. A welding flange of 5 mm, corresponding to the sealing area 3, is scheduled to be done on the final device.

According to a second example, the membrane 42 can be a microporous UHMWPE layer with a thickness of 200 microns. It is laminated/glued on a paper separation layer 43 of 40 GSM, that is also glued on the other side to a barrier layer 41 made of aluminium (20 microns) and PET (20 microns). The glue used can a polyurethane reactive hotmelt with a dosage of 15 GSM.

On the membrane side of this multilayer structure 4, a sealing portion 44 of thermoplastic material is applied. The material of the sealing portion 44 is preferably a polyolefin, and more preferably a polypropylene, although it would be clear for a person skill in the art that any alternative material can be used, with the limitation of having a sufficient chemical resistance in front of the substance that will be contained in the container and of having a melting range close to the temperature needed to be applied to seal the membrane 42 on the container 1.

The sealing portion 44 is applied following a closed pattern, corresponding to the sealing area 3, similar to the welding flange geometry of the container 1 where the multilayer structure 4 will be welded.

Preferably, the sealing portion 44 is not wider than the welding flange, but alternatively, the projection of the sealing portion 44 extends beyond what will be the welding flange of the container 1 sealed.

During the welding process of the multilayer structure 4 on the container 1, the sealing portion 44 is molten due to the heat of the welding tool and force to penetrate inside the microporous membrane 42 due to the pressure of the welding.

The result of this process is that the microporous membrane 42 is not anymore microporous in the sealing area 3 but is a heterophasic layer (membrane material+sealing portion material), avoiding transportation of the liquid.

Even though reference is made to a specific embodiment of the invention, it is apparent for a person skilled in the art that the device is susceptible of numerous variations and modifications, and all the details cited can be substituted by other technically equivalent ones, without departing from the scope of protection defined by the attached claims.

The invention claimed is:

1. A device for diffusion of volatile substances, the device comprising:
   a container for containing volatile substances, the container having an aperture and a perimetric flange at the perimeter of said aperture of the container defining a sealing area; and
   a multilayer structure placed over said aperture and on said perimetric flange, said multilayer structure comprising:
   a microporous membrane positioned over said aperture, and the perimetric flange, and having a section configured to permit the volatile substances contained in the container to diffuse through the microporous membrane, the microporous membrane including a heterophasic layer over the perimetric flange that does not permit liquid transport,
   a removable barrier layer removably attached to the microporous membrane; and
   a sealing portion on the perimetric flange and made of a material that extends into the microporous membrane to seal pores in the microporous membrane to define the heterophasic layer.

2. The device for diffusion of volatile substances according to claim 1, wherein said sealing portion is made from a polymeric material.

3. The device for diffusion of volatile substances according to claim 1, wherein said sealing portion is made from thermoset resin or thermoplastic.

4. The device for diffusion of volatile substances according to claim 1, wherein said multilayer structure comprises a separation layer that is placed between the barrier layer and the membrane, and that is removed before a first use.

5. The device for diffusion of volatile substances according to claim 1, wherein said barrier layer is made from metal or plastic.

6. The device for diffusion of volatile substances according to claim 4, wherein said separation layer is made from paper or plastic.

7. The device for diffusion of volatile substances according to claim 1, wherein said sealing portion is welded to said sealing area.

8. A device for diffusion of volatile substances, the device comprising:
- a container for containing volatile substances, the container having a perimeter and a perimeter flange in correspondence with the perimeter, and having an aperture and a sealing area in correspondence with the perimeter flange; and
- a multilayer structure placed on said aperture, said multilayer structure comprising:
- a microporous membrane positioned and configured such that the volatile substances contained in the container are diffused through the microporous membrane,
- a removable barrier layer; and
- a sealing portion made of a material and having a width and the sealing portion in contact with the sealing area, the width of the sealing portion corresponding with a width of the perimeter flange of the container.

\* \* \* \* \*